United States Patent
Reynolds

(10) Patent No.: US 11,520,890 B2
(45) Date of Patent: Dec. 6, 2022

(54) HARDWARE KEY SYSTEM FOR DEVICE PROTECTION

(71) Applicant: Ascensia Diabetes Care Holdings AG, Basel (CH)

(72) Inventor: Jeffery S. Reynolds, New Fairfield, CT (US)

(73) Assignee: Ascensia Diabetes Care Holdings AG, Basel (CH)

( * ) Notice: Subject to any disclaimer, the term of this patent is extended or adjusted under 35 U.S.C. 154(b) by 646 days.

(21) Appl. No.: 14/893,862

(22) PCT Filed: Oct. 23, 2014

(86) PCT No.: PCT/US2014/062013
§ 371 (c)(1),
(2) Date: Nov. 24, 2015

(87) PCT Pub. No.: WO2015/061595
PCT Pub. Date: Apr. 30, 2015

(65) Prior Publication Data
US 2016/0232315 A1    Aug. 11, 2016

Related U.S. Application Data

(60) Provisional application No. 61/895,924, filed on Oct. 25, 2013.

(51) Int. Cl.
*G06F 21/57* (2013.01)
*G06F 21/34* (2013.01)
*G16H 40/40* (2018.01)

(52) U.S. Cl.
CPC ............ *G06F 21/572* (2013.01); *G06F 21/34* (2013.01); *G16H 40/40* (2018.01)

(58) Field of Classification Search
CPC . A61B 5/14532; A61B 5/157; A61B 5/14546; A61B 5/1495; A61B 2562/0295;
(Continued)

(56) References Cited

U.S. PATENT DOCUMENTS 8,231,531 B2 * 7/2012 Brister .................. A61B 5/6832
600/309
8,842,001 B2 * 9/2014 Gilham .................. A61B 5/746
340/539.12

(Continued)

FOREIGN PATENT DOCUMENTS

CN      102369032 A       3/2012
EP             2499969 A1 *  9/2012   .......... A61B 17/3468
(Continued)

OTHER PUBLICATIONS 1001841.pdf,Michael J. McGrath and Cliodhna Ni Scanaill, Sensor Technologies, Healthcare, Wellness and Environmental Applications, Intel Lab Europe, Apress Open, pp. 35-36, Nov. 2013 (Year: 2013).*

(Continued)

*Primary Examiner* — Rachelle L Reichert
*Assistant Examiner* — Teresa S Williams
(74) *Attorney, Agent, or Firm* — Erise IP, P.A.

(57) ABSTRACT

A medical device includes at least one memory device storing data; a communication interface defining a first communication path to allow communications between the medical device and an external device or network; and a hardware key interface defining a second communication path that is separate from the first communication path. A hardware key is configured to be coupled to the meter via the second communication path defined by the hardware key interface. The data on the at least one memory device cannot be modified unless the hardware key interface is physically (Continued)

coupled to the hardware key. The hardware key may include a key code component and conducting lines, where the hardware key interface receives the key code via the conducting lines and the data on the at least one memory device cannot be modified unless the key code provided by the hardware key is validated.

20 Claims, 4 Drawing Sheets

(58) Field of Classification Search
CPC ... G01N 33/48792; G06F 8/65; G06F 1/3209; G06F 21/606; G06F 21/572; G06F 21/34; Y02A 90/26; G16H 40/40
USPC .......................................................... 705/2
See application file for complete search history.

(56) References Cited

U.S. PATENT DOCUMENTS

| | | |
|---|---|---|
| 2005/0222718 A1 | 10/2005 | Lazarz |
| 2008/0244717 A1 | 10/2008 | Jelatis |
| 2008/0300919 A1* | 12/2008 | Charlton ............... G16H 40/63 709/201 |
| 2010/0205454 A1 | 8/2010 | Wu et al. |
| 2010/0319436 A1 | 12/2010 | Sun |
| 2011/0179204 A1* | 7/2011 | Hulbert ................ G06F 3/0219 710/74 |
| 2011/0179405 A1* | 7/2011 | Dicks ..................... G06F 8/61 717/168 |
| 2011/0289497 A1* | 11/2011 | Kiaie ..................... G06F 8/65 717/171 |
| 2012/0203465 A1* | 8/2012 | Callewaert ............ G01N 33/53 702/19 |
| 2013/0188302 A1* | 7/2013 | Brown ................. G06Q 50/22 361/679.02 |
| 2014/0322815 A1* | 10/2014 | Carlsgaard ........... G01N 33/66 436/95 |

FOREIGN PATENT DOCUMENTS

| | | |
|---|---|---|
| JP | H 07-152553 A | 6/1995 |
| JP | 2001-224591 A | 8/2001 |
| JP | 2002-531827 A | 9/2002 |
| JP | 2007-054245 A | 3/2007 |
| JP | 2010-088925 A | 4/2010 |
| JP | 2012-507309 A | 3/2012 |
| JP | 2012-531948 A | 12/2012 |
| WO | WO 2015/061595 | 4/2015 |

OTHER PUBLICATIONS

International Search Report, PCT/US2014/062013, dated Jan. 8, 2015, (3 pages).
Written Opinion of the International Searching Authority, PCT/US2014/062013, dated Jan. 8, 2015, (7 pages).
Extended European Search Report, 18171161.5, dated Oct. 5, 2018, (10 pages).

* cited by examiner

HARDWARE KEY SYSTEM FOR DEVICE PROTECTION

CROSS-REFERENCE TO RELATED APPLICATIONS

This application is a nationalized application of Application No. PCT/US2014/062013 filed on Oct. 23, 2014, which claims the benefit of priority of Provisional Application No. 61/895,924 filed on Oct. 25, 2013, which are both incorporated by reference in their entireties.

FIELD OF THE INVENTION

The present invention relates generally to systems and methods for securing software, firmware, and/or other data stored on a device, and more particularly to systems and methods that require a hardware key to be coupled to a medical device before software, firmware, and/or other data stored on the medical device can be accessed by another device.

BACKGROUND OF THE INVENTION

The quantitative determination of analytes in body fluids is of great importance in the diagnoses and maintenance of certain physiological conditions. For example, individuals with diabetes frequently check the glucose level in their bodily fluids. The results of such tests can be used to regulate the glucose intake in their diets and/or to determine whether insulin or other medication needs to be administered.

Many diagnostic systems employ a meter to calculate the glucose value in a blood sample from an individual. Such meters operate by measuring an output, such as current or color, from a reaction with the glucose in the sample. The test results typically are displayed and stored by the meter. The meters store software, firmware, and/or other data that are accessed by a processor to perform measurements and/or provide other functions for the meter.

SUMMARY OF THE INVENTION

The embodiments described herein provide systems and methods for securing software, firmware, and/or other data (also collectively referred to herein as "data") stored on a medical device, such as a blood glucose meter. According to aspects of the present invention, systems and methods require a hardware key to be physically coupled to a medical device before data stored on the medical device can be accessed by an external device. The hardware key protects the data on the medical device from unauthorized access. Some embodiments may employ a hardware key in a process that allows an external device to update, upgrade, add, and/or delete data stored on the medical device. This modification process may be conducted during manufacturing of the medical device or when the medical device is returned to the manufacturer for maintenance. This modification process may also be conducted when the medical device is out in the field, i.e., in the possession of a user. As such, the modification process allows a manufacturer to manage the features of the medical device and to ensure that the medical device operates properly without requiring the user to send the medical device physically back to the manufacturer.

According to aspects of the present invention, for example, systems and methods employ a medical device and a hardware key. The medical device includes at least one memory device storing data; a communication interface defining a first communication path to allow communications between the medical device and an external device or network; and a hardware key interface defining a second communication path that is separate from the first communication path. The hardware key is configured to be coupled to the meter via the second communication path defined by the hardware key interface. The data on the at least one memory device cannot be modified unless the hardware key interface is physically coupled to the hardware key. The medical device may include a detector configured to detect the hardware key coupled to the hardware key interface. The hardware key may include a key code component and conducting lines, where the hardware key interface receives the key code via the conducting lines and the data on the at least one memory device cannot be modified unless the key code provided by the hardware key is validated.

In some embodiments, the medical device is a meter that determines an analyte concentration in a sample provided on a test sensor. The meter includes a test sensor port to receive the test sensor, and the test sensor port acts as the hardware key interface. In some cases, the meter further comprises a plurality of contacts configured to connect with electrodes on the test sensor and receive, via the electrodes, an electrochemical signal from a reaction between a reagent and the sample on the test sensor. The electrochemical signal indicates the analyte concentration. Additionally, the plurality of contacts may be configured to connect with conducting lines on the test sensor and receive, via the conducting lines, a calibration code corresponding to the reaction between the reagent and the sample on the test sensor. The plurality of contacts are further configured to receive a key code from the hardware key, where the data on the at least one memory device cannot be modified unless the key code provided by the hardware key is validated.

Still other aspects, features, and advantages of the present invention are readily apparent from the following detailed description, by illustrating a number of exemplary embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive. The invention is to cover all modifications, equivalents, and alternatives falling within the spirit and scope of the invention.

DESCRIPTION

The embodiments described herein provide systems and methods for securing software, firmware, and/or other data (also collectively referred to herein as "data") stored on a medical device, such as a blood glucose meter. According to aspects of the present invention, systems and methods require a hardware key to be physically coupled to a medical device before data stored on the medical device can be accessed by an external device. The hardware key protects the data on the medical device from unauthorized access. Some embodiments may employ a hardware key in a process that allows an external device to update, upgrade, add, and/or delete data stored on the medical device. This modification process may be conducted during manufacturing of the medical device or when the medical device is returned to the manufacturer for maintenance. This modification process may also be conducted when the medical device is out in the field, i.e., in the possession of a user. As such, the modification process allows a manufacturer to manage the features of the medical device and to ensure that the medical device operates properly without requiring the user to send the medical device physically back to the manufacturer.

Figure 1:
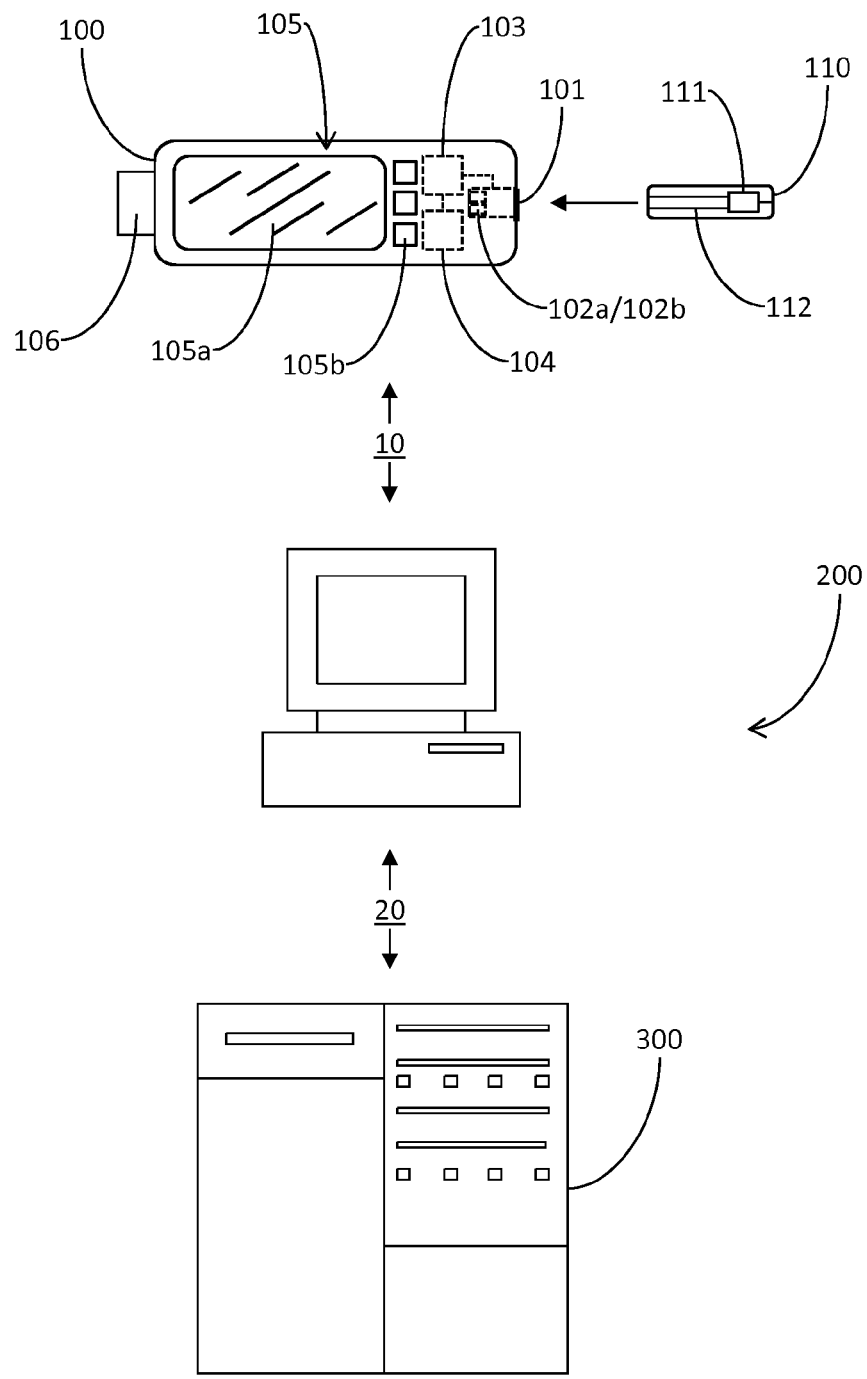
FIG. 1 illustrates an example system that includes a medical device, a computing device, and a server, which are described to demonstrate aspects of the present invention.

Referring to FIG. 1, a meter 100 is described to illustrate aspects of the present invention. As shown in FIG. 1, the meter 100 receives a test sensor 110 into a test sensor port 101. The test sensor 110 is configured to receive a fluid sample, which has an analyte that is analyzed by the meter 100. For the sake of discussion, the meter 100 in this example is a blood glucose meter that provides point-in-time measurements of blood glucose concentrations in blood samples received on the test sensor 110.

As shown in FIG. 1, the test sensor 110 may be an electrochemical test sensor. As such, the test sensor 110 includes a receiving area 111 that contains a reagent that reacts with the sample to provide information relating to an analyte in the sample, i.e., blood glucose concentration. Specifically, the reagent converts the glucose in the sample into a chemical species that is electrochemically measurable and reflects the concentration of glucose in the sample. The test sensor 110 also includes a plurality of electrodes 112 that transmits the measurable electrical signal from the electrochemical reaction.

Correspondingly, the meter 100 includes contacts 102*a* that contact the electrodes 112 on the test sensor 110 to receive the electrical signal from the electrodes 112. The meter 100 employs a processing component 103 to process the electrical signal and determine a glucose concentration measurement. The processing component 103, for example, may include an analog front end that interfaces with the contacts 102 to receive an analog signal from the test sensor 110 and a back end digital engine to digitally process the signal. The processing component 103 includes one or more computer processors that execute programmed instructions according to a measurement algorithm. The programmed instructions are stored in, and read from, at least one memory device 104. The memory device 104, for example, may include any type or combination of computer readable and writable storage devices. For example, the memory device 104 may be non-volatile memory, such as flash memory, or the like.

In general, the processing component 103 may execute programmed instructions stored as data on the memory device 104. The programmed instructions provide various functions for the meter 100 and control various aspects of the operation of the meter 100. For example, the meter 100 may include a user interface 105 which provides a graphical user interface (GUI) 105*a* and user-operated controls 105*b*. The display 105*a* may present information relating to the test results, the testing procedure, etc., as well as other responses to user inputs, etc. Accordingly, the processing component 103 may execute programmed instructions to show information on the GUI 105*a*.

The memory device 104 may also store program parameters, constants, lookup tables, etc., that are employed by the processing component 103 when executing the programmed instructions. The program parameters, for example, may alter operation of the meter 100 according to geographical or market considerations. In general, the memory device 104 stores software, firmware, and other data that are used for the operation of the meter 100.

As shown in FIG. 1, the meter 100 can be communicatively coupled to an external computing device 200 via a wired or wireless connection 10. The computing device 200 may be a desktop or laptop personal computer, a handheld or pocket personal computer, a computer tablet, a smart phone/device, a personal data assistant (PDA), or any other device that includes processing capabilities and other features that can be employed with the meter 100. Although the meter 100 can run a testing procedure to produce test results and present related information on the GUI 105*a*, the computing device 200 can provide more advanced functionality for managing, processing, and displaying test results and related information. For example, the computing device 200 has the necessary processing power, program memory (e.g., RAM), and display capabilities to execute health data management software that provides more advanced analysis and presentation of the test results measured by the meter 100. For instance, the computing device 200 may download test results from the meter 100, perform complex statistical analysis on the test results, and display the statistical analysis as graphs on a high-resolution GUI provided by the computing device 200.

As shown in FIG. 1, the meter 100 includes a communication interface 106 that allows the meter 100 to be wire connected to the computing device 200, for example, via Universal Serial Bus (USB), RS-232, open-collector, or other protocol. The communication interface 106, for example, may be plugged directly into the computing device 200, e.g., into a USB port, or may receive a communication cable that extends between the meter 100 and the computing device 200. Alternatively or additionally, the meter 100 may communicate wirelessly with the computing device 200, for example, via a radio-frequency (RF) link (e.g., a short-range RF telemetry), such as Bluetooth® wireless technologies, Zigbee, Z-Sense™ technology, FitSense, BodyLAN™ system, and other RF technologies. Other wireless, communication technologies, such as infrared (IR) links, also may be used. In general, the wired or wireless connection 10 employs any technology that allows data to be exchanged between the meter 100 and the computing device 200.

The computing device 200 can, in turn, be communicatively coupled to other external systems over a network, such as the Internet, a local/wide area network (LAN/WAN), a cloud network, a cellular network, etc. For example, the computing device 200 may be coupled to the network via a wired connection, e.g., Ethernet connection, or a wireless connection, e.g., via Wi-Fi such as a broadband wireless hot spot. The external systems may provide other functions for the meter 100. For example, the computing device 200 may access a tele-health system that allows the meter 100 to share test results with healthcare professionals or other diagnostic systems at remote locations. As shown in FIG. 1, the computing device 200 is communicatively coupled, via a wired or wireless connection 20, to a server system 300 that is associated with the manufacturer of the meter 100 (or authorized third party). As such, the meter 100 can exchange data with the manufacturer of the meter 100. In alternative embodiments, the meter 100 can be communicatively coupled to the server system 300 without the computing device 200. In some cases, the meter 100 is equipped to connect to a network to communicate with the server system 300. In other cases, the meter 100 may be connected locally with the server system 300, for example, during manufacturing or when the meter is returned to the manufacturer for maintenance.

It is understood that the communication architecture illustrated in FIG. 1 is merely provided as an example to illustrate aspects of the present invention. The wired or wireless technologies and networks described above are also only provided as examples. In general, according to aspects of the present invention, any medical device may include a communication interface that employs any combination of wired and/or wireless technologies to allow data to be exchanged between the medical device and one or more external devices, which may or may not reside on one or more networks.

As described above, the memory device 104 of the meter 100 stores software, firmware, and/or other data required for the calculation of test results and operation of the meter 100. In some cases, the data in the memory device 104 can be updated, or patched, with newer versions to fix errors/bugs and to ensure that the meter 100 operates properly. In other cases, the data in the memory device 104 can be modified to upgrade, reconfigure, or customize the features provided by the meter 100. In yet other cases, data can be added to the memory device 104 to provide new features on the meter 100, thereby making the latest features available to users who already possess the meter 100. In other cases, new data can be employed to make the existing meter 100 compatible with other newly released accessories or devices. For example, if the meter 100 uses a test sensor to test blood for blood glucose concentration and the manufacturer develops a new test sensor that improves accuracy or test time, embodiments would allow the user to upgrade the data so that the meter 100 is capable of reading the new test sensor. Accordingly, by allowing the meter 100 to communicate with the manufacturer's server system 300, the manufacturer can update, upgrade, add, and/or delete the data stored in the memory device 104 even if the medical device 100 is already in the possession of the user.

The manufacturer's server system 300 stores code and/or other data that can be transmitted, e.g., over the connections 10, 20, to the meter 100. Programs on the server system 300, the computing device 200, the meter 100, or any combination thereof, may manage aspects of the modification process. Advantageously, the modification process can be triggered and conducted electronically in an online self-serve process that does not require the user to contact the manufacturer for direct personal assistance. For example, if a government regulatory agency requires a recall of the meter 100 to correct a problem, users can correct the problem on their own through the online self-serve process without having to send the meter 100 to the manufacturer.

The communication between the meter 100 and the server system 300 is described herein to illustrate aspects of the present invention. In general, it is understood that aspects of the present invention can be employed when any medical device is communicatively coupled to any external device(s), which may or may not reside on one or more networks.

Due to the important medical functions associated with the meter 100, embodiments may employ validation procedures to ensure that the modification process has not corrupted the data stored on the meter 100 and that the meter 100 operates properly. For additional data security, the entry of user ID's/passwords, personal identification numbers (PIN's), and/or other authorization codes may be required to initiate the modification process. Furthermore, the modification process may employ encryption/decryption techniques for the exchange of data between the meter 100 and server system 300.

Although digital techniques may be employed to add some security to communications between a meter and an external device, e.g., the server system 300 on a network, the meter may be susceptible to digital access and unauthorized modification or corruption of data stored on the meter. Although the connectivity capabilities of the meter may provide beneficial features such as those described above, the connectivity may leave the meter open to unauthorized tampering or corruption if the digital security techniques fail. Aspects of the present invention, however, minimize the susceptibility of medical devices to such tampering or corruption.

Figure 2A:
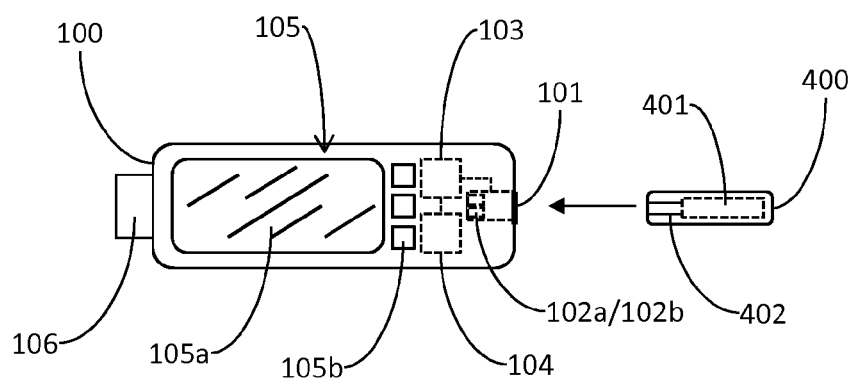
FIG. 2A illustrates an example hardware key that is employed with the medical device of FIG. 1, according to aspects of the present invention.
Figure 2B:
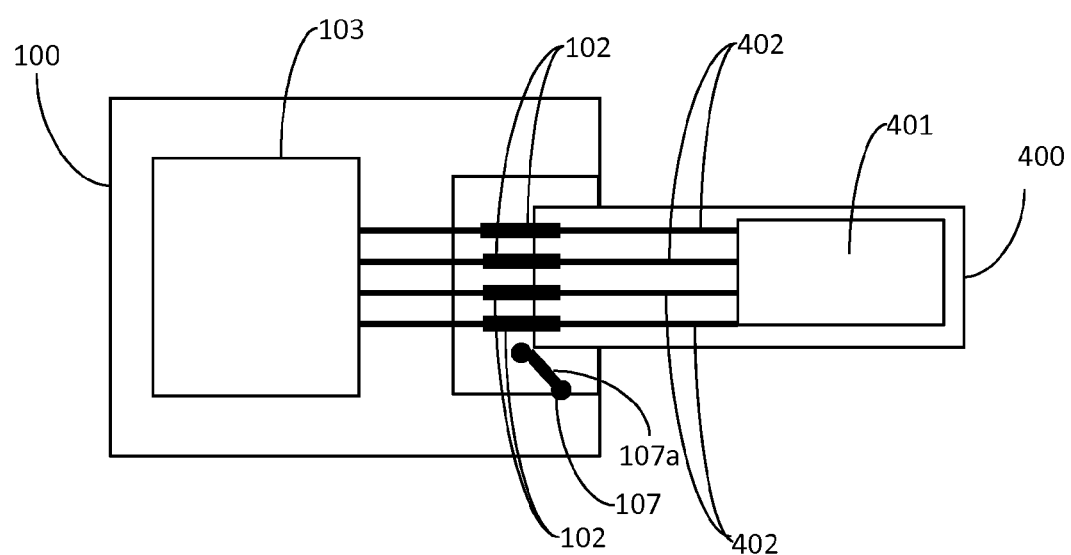
FIG. 2B further illustrates the example hardware key and medical device of FIG. 2A, according to aspects of the present invention.

In particular, aspects of the present invention require a hardware key to be physically coupled to a medical device before access is granted to its data. The physical connection between the hardware key and the medical device generally requires local physical access to the medical device and cannot be spoofed digitally. For example, FIGS. 2A-B illustrate a hardware key 400 that can be combined with the meter 100. In particular, the hardware key 400 is configured to be received by the port 101 which typically receives test sensors 110 as shown in FIG. 1. The hardware key 400 has a shape and dimensions that are sufficiently similar to the test sensor 110 to permit compatibility with the port 101.

As FIG. 2B illustrates more clearly, the hardware key 400 includes a key code component 401 and a plurality of conducting lines 402. The key code component 401 provides a pre-programmed (static or dynamic) set of signals which are transmitted to the meter 100 via the conducting lines 402. When the hardware key 400 is received into the port 101, the contacts 102a of the meter 100 may connect with the conducting lines 402 to receive the signals from the key code component 401. In addition to having contacts 102a that can receive analog signals from the electrochemical reaction on the test sensor 110, the meter 100 may also include additional contacts 102b for receiving calibration codes from conducting lines on the test sensor 110. The calibration codes calibrate the measurement algorithm to account for variations in the reagent that are used on the test sensors 110. Any combination of the contacts 102a or 102b may be used to connect with the conducting lines 402 of the hardware key 400. The conductive connection between the meter 100 and the hardware key 400 also allows the electronic component 401 to draw any necessary electrical power from a power source in the meter 100, e.g., a battery.

The meter 100 is able to detect the hardware key 400 when it is inserted into the port 101. As shown in FIG. 2B, the meter 100 includes a detector 107 to detect the test sensor 110 when it is received into the port 101. The detector 107 may be similarly employed to detect the hardware key 400 when it is received into the port 101. As the hardware key 400 moves into the port 101, the hardware key 400 may contact a conductive moving component 107a of the detector 107. In response, the conductive moving component 107a moves, e.g., pivots, to close an electrical circuit in the meter 100 signaling the presence of the hardware key 400 and allowing access to the data stored on the memory device 104. Additionally, the conducting lines 402 of the hardware key 400 may connect with the contacts 102a and/or contacts 102b of the meter 100 to close a specific electrical circuit that uniquely identifies the hardware key 400 and distinguishes the hardware key 400 from a test sensor 110.

Figure 3:
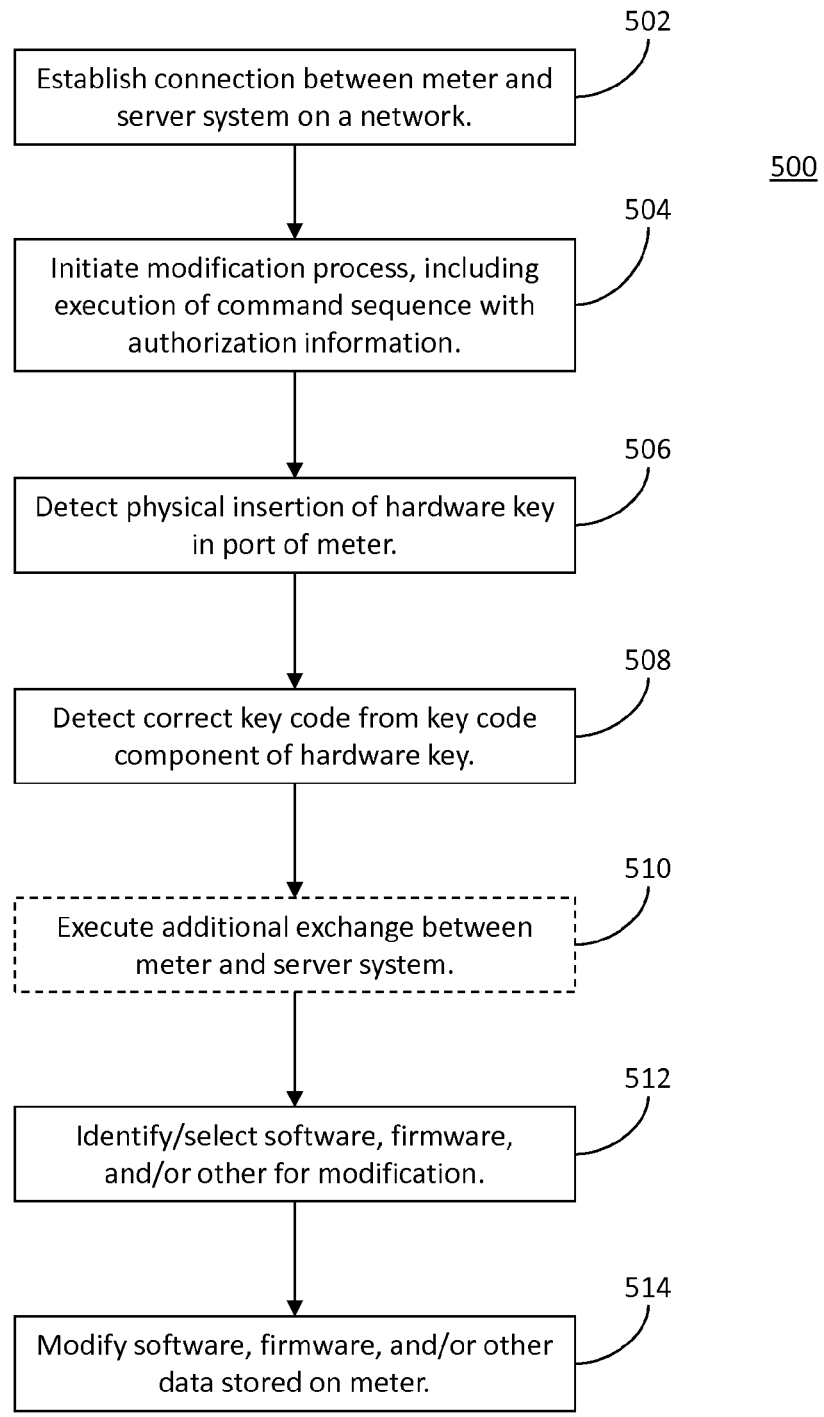
FIG. 3 illustrates an example method for employing the hardware key and meter of FIGS. 2A-B, according to aspects of the present invention.

As illustrated in the example embodiment of FIG. 3, communication is established in act 502 between the meter 100 and the server system 300 on a network or other connection. In some cases, for example, the meter 100 may communicate with the server system 300 via the computing device 200, as shown in FIG. 1. In other cases, the meter 100 may communicate more directly with the server system 300. The modification process is then initiated in act 504, e.g., automatically upon establishing communication in act 502 or manually by entering a command sequence via the meter 100, the computing device 200, or the server system 300. The command sequence may require the entry of user ID's/passwords, personal identification numbers (PINs), and/or other authorization codes to identify the meter 100 and establish digital authorization for the exchange of data between the meter 100 and the server system 300. The command sequence may be automatically or manually executed. Before any data stored on the meter 100 can be accessed and modified, however, the meter 100 in act 506 must also detect the hardware key 400 in the port 101. In the embodiment of FIG. 3, the hardware key 400 is used in combination with digital security techniques, e.g., entry of user ID's/passwords, etc. Additionally, the correct pre-programmed set of signals from the key code component 401 must be transmitted to the meter 100 in act 508. The hardware key 400 must be physically coupled to the meter 100 before the modification process is permitted to proceed. To add further security, additional handshaking or other exchanges between the meter 100 and the server system 300 may be required in optional act 510. Once the meter 100 has been properly identified and access to the meter 100 is permitted with the hardware key 400, the modifications, e.g., updates, upgrades, and/or additions, are identified/selected in act 512. And the data stored in the memory device 104 of the meter 100 is correspondingly modified in act 514. In some cases, modifications are executed automatically, e.g., for critical bug fixes or regulatory compliance updates. In other cases, modifications are executed only after user approval, e.g., for optional convenience features. A version management program may be employed to determine what software, firmware, and/or other data on the meter 100 is compatible with, and can be replaced by, newer or different versions stored on the server system 300.

In some embodiments, the data B from the server system 300 is downloaded to an area of the memory device 104 that is separate from the area storing the pre-existing data A being employed by the meter 100. An area of memory may be specifically dedicated for the modification process. In other words, the data A is retained, rather than deleted or overwritten, at least until the complete download of data B has been verified and a validating system check has been successfully completed. If the download and system check are successful, data B is deployed for regular operation. If the download and system check are unsuccessful, however, data A is still available and provides a recovery or restore option. The data B is removed when the modification process fails. In some embodiments, the data A is retained even after the data B is deployed to give users the option to restore the data A.

By allowing the hardware key 400 to be received into the port 101 as shown in FIGS. 1B and 1C, the embodiments above provide a particularly cost-effective and convenient solution. The meter 100 does not have to be structurally reconfigured to accommodate the hardware key 400. By using the port 101, embodiments take advantage of components that already exist in the original meter design, e.g., the contacts 102a, the contacts 102b, the detector 107, etc. No changes are required to existing meter hardware designs. Furthermore, the port 101 for the hardware key 400 establishes a communication path with the meter 100 that is separate from communications via the interface element 106.

As described above, the key code component 401 provides a pre-programmed (static or dynamic) set of key code signals which are transmitted to the meter 100 via the conducting lines 402. The key code component 401 may be any device that provides a key code that can be transmitted to the meter 100 to identify the hardware key 400. In one embodiment, the conducting lines 402 on the hardware key 400 may be configured like the test sensor 110 so that it can communicate a specific calibration code (not used with the test sensor 110) to the contacts 102b as a static key code. Or in another embodiment, the hardware key 400 may cycle through a series of calibration codes to provide a different (dynamic) key code to the contacts 102b each time it is interrogated. Or in yet another embodiment, the conducting lines 402 on the hardware key 400 may produce a resistance within a fixed range which is transmitted to the contacts 102a as the key code; such a system may be employed with meters 100 that do not include contacts 102b for receiving calibration codes or a detector 107. In general, embodiments may use any combination of the contacts 102a and 102b to receive any combination of static or dynamic calibration codes, analog resistance signals, etc., as key codes from the hardware key 400.

Figure 4:
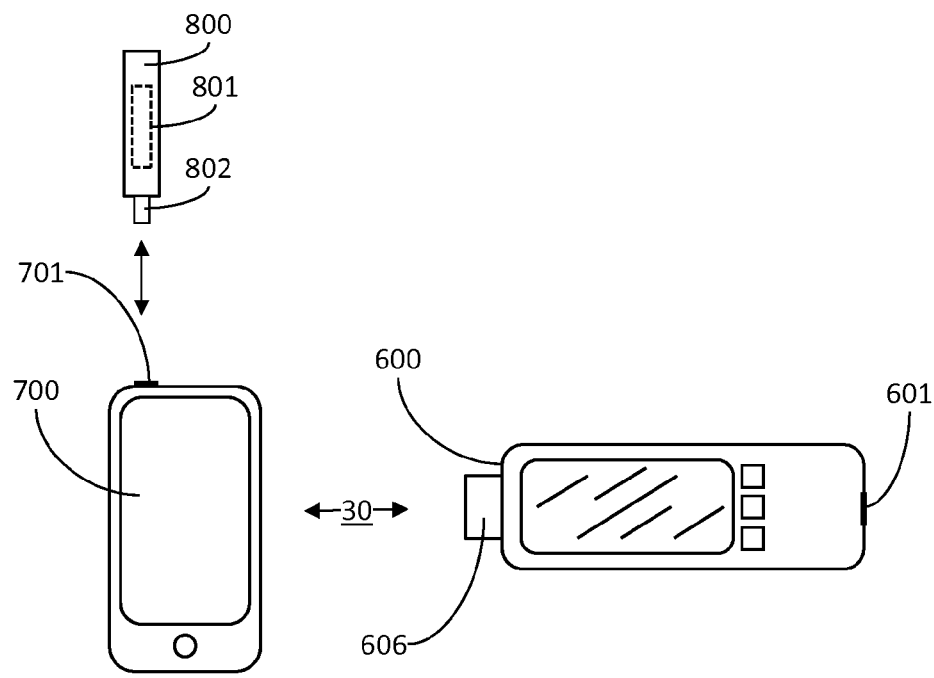
FIG. 4 illustrates another example hardware key that is employed with a medical device, according to aspects of the present invention.

It is understood that other embodiments may employ other approaches to couple the hardware key to the medical device. In general, to receive a hardware key code, aspects of the present invention may employ any analog or digital input/interface that is separate from the communication path to external devices or networks. For example, as shown in FIG. 4, a meter 600 is communicatively coupled to a smart phone 700 via a wireless or wired connection 30, e.g., using a communication interface 606. While the smart phone 700 provides wireless connectivity to a network, e.g., Wi-Fi network, cellular network, etc., it provides another communication path to transmit a key code to the meter 600. For instance, the smart phone 700 includes a microphone input (jack) 701 which can be employed to receive a hardware key 800 which provides an analog key code. The hardware key 800 may include a key code component 801 that determines a key code that is transmitted to the smart phone 700 via connector 802, and then onto the meter 600. The analog input through the microphone input 701 ensures that the key code cannot be digitally remotely spoofed. Advantageously, the embodiment of FIG. 4 takes advantage of components that already exist in the original meter and smart phone designs. The original hardware design of the meter 600 and the smart phone 700 do not have to be modified.

Figure 5:
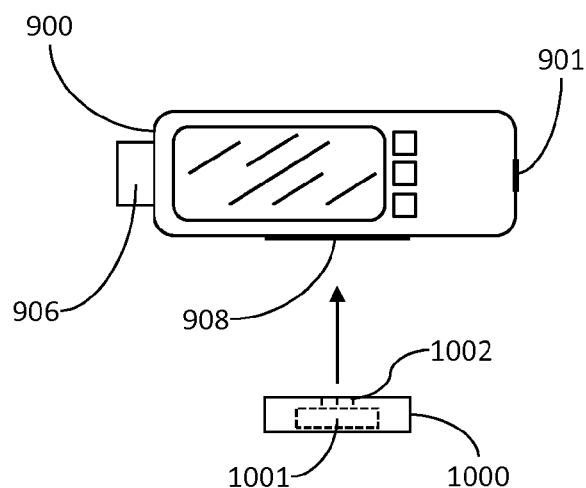
FIG. 5 illustrates yet another example hardware key that is employed with a medical device, according to aspects of the present invention.

It is also understood that embodiments are not limited to the use of existing hardware to employ aspects of the present invention. For example, as shown in the example of FIG. 5, rather than using a test sensor port 901 to receive a hardware key 1000, a meter 900 includes an additional key port 908 that is specifically configured to receive the hardware key 1000. The hardware key 1000 may be similar to the hardware key 400 described above. For example, the hardware key 1000 may include a key code component 1001 that determines a key code that is transmitted to the meter 900 via conducting lines 1002. As shown in FIG. 5, the meter 900 also includes a communication interface 906. Similar to the embodiments described above, the port 908 for the hardware key 1000 establishes a communication path with the meter 900 that is separate from communications via the interface element 906.

In alternative embodiments, the hardware key may be physically integrated with, and more permanently coupled to, the meter. The hardware key and the meter may operate similar to the embodiments above to secure the data on the meter. Instead of inserting the hardware key into a port, however, the communication path between the meter and the hardware key can be established, for example, by manually operating a switch. The hardware key in these alternative embodiments may include a key code component and conducting lines to transmit a key code to other processing circuitry in the meter when the hardware key is switched on. The communication path between the meter and the hardware key is separate from other communication interfaces for the meter.

Although the examples above may be described with respect to a modification process that occurs after the medical device is already in the possession of a user (i.e., out in the field), the modification process may be conducted during manufacturing of the medical device or when the medical device is returned to the manufacturer for maintenance. In other words, the hardware key must be coupled to the medical device as described above before any programming system can transmit software, firmware, and/or other data to the memory of the medical device during manufacturing.

In general, by requiring a hardware key to be physically coupled to a medical device to permit access, aspects of the present invention protect the integrity of software, firmware, and/or other data on the medical device while still allowing the medical device to be connected to external systems which can enhance the use of the medical device. Rather than relying solely on a digital modification process through a conventional communication interface connecting the meter to external systems, a separate port (an analog or mixed signal port) is additionally required to receive the hardware key. In other words, communication with the hardware key is not associated with digital access via the conventional communication interface. Advantageously, requiring the hardware key prevents unauthorized access to data on a medical device across a network or other communications connection, because even if the digital security fails, the data on the meter cannot be accessed without the hardware key and physical access to the medical devices.

Although the meters described in embodiments above may relate to the measurement of glucose concentration, other embodiments may measure the concentration of other analytes in the fluid sample. Analytes that may be analyzed include glucose, lipid profiles (e.g., cholesterol, triglycerides, LDL and HDL), microalbumin, hemoglobin $A_1C$, fructose, lactate, or bilirubin. The analytes may be in a whole blood sample, a blood serum sample, a blood plasma sample, other body fluids like ISF (interstitial fluid) and urine, and non-body fluids. Moreover, it is understood that other medical devices or non-medical electronic devices may employ aspects of the present invention to maintain data security.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

The invention claimed is:

1. A medical device, comprising:
   at least one memory device;
   at least one processor;
   a test sensor port configured to receive a hardware key at a first timeframe and a test sensor at a second timeframe;
   electrical circuitry electrically coupling the test sensor port to the at least one processor, the electrical circuitry configured to receive (i) a hardware key signal from the hardware key when the hardware key is inserted in the test sensor port, and (ii) a test sensor signal from the test sensor when the test sensor is inserted in the test sensor port,
   wherein the test sensor signal from the test sensor corresponds to an electrochemical reaction between a reagent and a sample containing an analyte on or within the test sensor;
   a detector switch electrically coupled to the at least one processor for identifying a first switch-state and a second switch-state,
   wherein the first switch-state indicates an absence of the hardware key in the test sensor port, and the second switch-state indicates a presence of the hardware key in the test sensor port; and
   a wireless communication interface configured to receive wireless communications from an external device or network during the presence of the hardware key in the test sensor port indicated by the second switch-state;
   wherein the at least one memory device comprises data stored thereon, wherein the data comprises computer-executable instructions, which, when executed by the at least one processor, cause the at least one processor to perform operations of the medical device, the operations comprising:
   (i) responsive to the first switch-state indicating the absence of the hardware key, preventing a modification to the data stored on the at least one memory device;
   (ii) responsive to the hardware key signal from the hardware key at the first timeframe occurring concurrently with the second switch-state indicating the presence of the hardware key in the test sensor port, receiving a wireless communication via the wireless communication interface and modifying the data stored on the at least one memory device,
   wherein at least one of receiving the wireless communication and modifying the data is contingent upon the wireless communication having been received during the presence of the hardware key in the test sensor port indicated by the second switch-state; and
   (iii) responsive to the test sensor signal from the test sensor at the second timeframe, performing a method of determining an analyte concentration of the analyte in the sample based at least in part on the test sensor signal from the test sensor, wherein the wireless communication received during the presence of the hardware key in the test sensor port comprises an update to the method of determining the analyte concentration, wherein modifying the data comprises updating data associated with the method, and wherein the method is performed at the second timeframe based at least in part on the update.

2. The medical device of claim 1, wherein the medical device comprises a meter configured to determine the analyte concentration, wherein the analyte comprises blood glucose and the sample comprises blood.

3. The medical device of claim 2, wherein the electrical circuitry comprises a plurality of contacts configured to electrically connect with a first plurality of electrodes on the hardware key or with a second plurality of electrodes on the test sensor, wherein the electrical circuitry is configured to receive the hardware key signal from the hardware key via the first plurality of electrodes when contacting the plurality of contacts, and wherein the electrical circuitry is configured to receive the test sensor signal from the test sensor via the second plurality of electrodes when contacting the plurality of contacts, wherein the hardware key signal comprises a key code from the hardware key, and wherein the operations further comprise:
determining a validity of the key code, and, responsive to the validity of the key code having been determined, receiving the wireless communication via the wireless communication interface and modifying the data stored on the at least one memory device, wherein at least one of receiving the wireless communication and modifying the data is contingent upon the validity of the key code having been determined during the presence of the hardware key in the test sensor port indicated by the second switch-state.

4. The medical device of claim 3, wherein the hardware key comprises conducting lines that provide a resistance to the hardware key signal, the resistance detectable from the hardware key signal propagating through the plurality of contacts, wherein the key code is defined at least in part by the resistance of the hardware key signal.

5. The medical device of claim 2, wherein the test sensor signal from the test sensor comprises a calibration code configured to compensate for a variation in the reagent, wherein the operations further comprise:
determining the calibration code, and based at least in part on the calibration code, compensating for the variation in the reagent when performing the method of determining the analyte concentration of the analyte in the sample.

6. The medical device of claim 1, wherein the operations further comprise:
validating a key code based at least in part on the hardware key signal from the hardware key, and responsive to validating the key code, receiving the wireless communication via the wireless communication interface and modifying the data stored on the at least one memory device;
wherein the update comprises an update to software and/or firmware.

7. The medical device of claim 1, wherein the medical device comprises a meter configured to determine the analyte concentration;
wherein the hardware key signal comprises a key code from the hardware key, and wherein the operations further comprise:
transmitting the key code to the meter, and
responsive to the meter having received the key code, performing the method of determining the analyte concentration of the analyte in the sample.

8. A medical device system, comprising:
a medical device and a hardware key;
wherein the medical device comprises:
at least one memory device;
at least one processor;
a test sensor port configured to receive the hardware key at a first timeframe and a test sensor at a second timeframe;
electrical circuitry electrically coupling the test sensor port to the at least one processor, the electrical circuitry configured to receive a hardware key signal from the hardware key when the hardware key is inserted in the test sensor port, and the electrical circuitry configured to receive a test sensor signal from the test sensor when the test sensor is inserted in the test sensor port, wherein the test sensor signal from the test sensor corresponds to an electrochemical reaction between a reagent and a sample containing an analyte on or within the test sensor;
a detector switch electrically coupled to the at least one processor, the detector switch configured to physically move from a first position corresponding to a first switch-state to a second position corresponding to a second switch-state when the hardware key is inserted in the test sensor port, the first switch-state indicating an absence of the hardware key in the test sensor port and the second switch-state indicating a presence of the hardware key in the test sensor port; and
a wireless communication interface configured to receive wireless communications from an external device or network during the presence of the hardware key in the test sensor port indicated by the second switch-state;
wherein the at least one memory device comprises data stored thereon, wherein the data comprises computer-executable instructions, which, when executed by the at least one processor, cause the at least one processor to perform operations of the medical device, the operations comprising:
(i) responsive to the first switch-state indicating the absence of the hardware key, preventing a modification to the data stored on the at least one memory device;
(ii) responsive to the hardware key signal from the hardware key at the first timeframe occurring concurrently with the second switch-state indicating the presence of the hardware key in the test sensor port, receiving a wireless communication via the wireless communication interface and modifying the data stored on the at least one memory device, wherein at least one of receiving the wireless communication and modifying the data is contingent upon the wireless communication having been received during the presence of the hardware key in the test sensor port indicated by the second switch-state; and
(iii) responsive to the test sensor signal from the test sensor at the second timeframe, performing a method of determining an analyte concentration of the analyte in the sample based at least in part on the test sensor signal from the test sensor;

wherein the wireless communication received during the presence of the hardware key in the test sensor port comprises an update to the method of determining the analyte concentration, wherein modifying the data comprises updating data associated with the method, and wherein the method is performed at the second timeframe based at least in part on the update.

9. The medical device system of claim 8, wherein the medical device comprises a meter configured to determine the analyte concentration, wherein the analyte comprises blood glucose and the sample comprises blood.

10. The medical device system of claim 9, wherein the electrical circuitry comprises a plurality of contacts configured to electrically connect with a first plurality of electrodes on the hardware key or with a second plurality of electrodes on the test sensor, wherein the electrical circuitry is configured to receive the hardware key signal from the hardware key via the first plurality of electrodes when contacting the plurality of contacts, and wherein the electrical circuitry is configured to receive the test sensor signal from the test sensor via the second plurality of electrodes when contacting the plurality of contacts, wherein the hardware key signal comprises a key code from the hardware key, and
wherein the operations further comprise:
determining a validity of the key code, and, responsive to the validity of the key code having been determined, receiving the wireless communication via the wireless communication interface and modifying the data stored on the at least one memory device, wherein at least one of receiving the wireless communication and modifying the data is contingent upon the validity of the key code having been determined during the presence of the hardware key in the test sensor port indicated by the second switch-state.

11. The medical device system of claim 10, wherein the hardware key comprises conducting lines that provide a resistance to the hardware key signal, the resistance detectable from the hardware key signal propagating through the plurality of contacts, wherein the key code is defined at least in part by the resistance of the hardware key signal.

12. The medical device system of claim 9, wherein the test sensor signal from the test sensor comprises a calibration code configured to compensate for a variation in the reagent, wherein the operations further comprise:
determining the calibration code, and based at least in part on the calibration code, compensating for the variation in the reagent when performing the method of determining the analyte concentration of the analyte in the sample.

13. The medical device system of claim 8, wherein the operations further comprise:
validating a key code based at least in part on the hardware key signal from the hardware key, and responsive to validating the key code, receiving the wireless communication via the wireless communication interface and modifying the data stored on the at least one memory device;
wherein the update comprises an update to software and/or firmware.

14. The medical device system of claim 8, wherein the medical device comprises a meter configured to determine the analyte concentration;
wherein the hardware key signal comprises a key code from the hardware key, and wherein the operations further comprise:
transmitting the key code to the meter, and
responsive to the meter having received the key code, performing the method of determining the analyte concentration of the analyte in the sample.

15. A method of operating a medical device, the method comprising:
determining, with at least one processor of the medical device, a first switch-state of a detector switch electrically coupled to the at least one processor, the first switch-state indicating an absence of a hardware in in a test sensor port of the medical device, the test sensor port configured to receive a hardware key at a first timeframe and a test sensor at a second timeframe;
responsive to the at least one processor determining the first switch-state, preventing a modification to data stored on at least one memory device of the medical device;
determining, with the at least one processor, a second switch-state of the detector switch, the second switch-state indicating a presence of the hardware key in the test sensor port, the detector switch configured to physically move from a first position corresponding to the first switch-state to a second position corresponding to the second switch-state when the hardware key is inserted in the test sensor port;
determining, with the at least one processor, a hardware key signal from the hardware key when the hardware key is inserted in the test sensor port at the first timeframe, the first timeframe occurring concurrently with the second switch-state, the hardware key signal received via electrical circuitry coupling the test sensor port to the at least one processor, and the electrical circuitry configured to receive the hardware key signal from the hardware key when the hardware key is inserted in the test sensor port;
responsive to the at least one processor determining the hardware key signal from the hardware key at the first timeframe concurrently with the second switch-state indicating the presence of the hardware key in the test sensor port, receiving a wireless communication via a wireless communication interface from an external device or network and modifying the data stored on the at least one memory device, wherein at least one of receiving the wireless communication and modifying the data is contingent upon the wireless communication having been received during the presence of the hardware key in the test sensor port indicated by the second switch-state, the wireless communication interface configured to receive the wireless communication during the presence of the hardware key in the test sensor port indicated by the second switch-state;
determining, with the at least one processor, a test sensor signal from the test sensor when the test sensor is inserted in the test sensor port at the second timeframe, wherein the test sensor signal from the test sensor corresponds to an electrochemical reaction between a reagent and a sample containing an analyte on or within the test sensor;
responsive to the at least one processor determining the test sensor signal from the test sensor at the second timeframe, performing a method of determining an analyte concentration of the analyte in the sample based at least in part on the test sensor signal from the test sensor;
wherein the wireless communication received during the presence of the hardware key in the test sensor port comprises an update to the method of determining the analyte concentration, wherein modifying the data comprises updating data associated with the method, and wherein the method is performed at the second timeframe based at least in part on the update.

16. The method of claim 15, wherein the hardware key signal comprises a key code from the hardware key, and wherein the method further comprises:
   determining a validity of the key code, and, responsive to the validity of the key code having been determined, receiving the wireless communication via the wireless communication interface and modifying the data stored on the at least one memory device;
   wherein at least one of receiving the wireless communication and modifying the data is contingent upon the validity of the key code having been determined during the presence of the hardware key in the test sensor port indicated by the second switch-state.

17. The method of claim 16, wherein the hardware key comprises conducting lines that provide a resistance to the hardware key signal, wherein the key code is defined at least in part by the resistance of the hardware key signal, and wherein the method further comprises:
   determining the resistance of the hardware key signal and determining the key code based at least in part on the resistance of the hardware key signal.

18. The method of claim 15, wherein the medical device comprises a meter configured to determine the analyte concentration, wherein the analyte comprises blood glucose and the sample comprises blood.

19. The method of claim 18, wherein the electrical circuitry comprises a plurality of contacts configured to electrically connect with a first plurality of electrodes on the hardware key or with a second plurality of electrodes on the test sensor, wherein the electrical circuitry is configured to receive the hardware key signal from the hardware key via the first plurality of electrodes when contacting the plurality of contacts, and wherein the electrical circuitry is configured to receive the test sensor signal from the test sensor via the second plurality of electrodes when contacting the plurality of contacts, wherein the hardware key signal comprises a key code from the hardware key, wherein the method further comprises:
   determining a validity of the key code, and, responsive to the validity of the key code having been determined, receiving the wireless communication via the wireless communication interface and modifying the data stored on the at least one memory device, wherein at least one of receiving the wireless communication and modifying the data is contingent upon the validity of the key code having been determined during the presence of the hardware key in the test sensor port indicated by the second switch-state.

20. The method of claim 18, wherein the test sensor signal from the test sensor comprises a calibration code configured to compensate for a variation in the reagent, wherein the method further comprises:
   determining the calibration code, and based at least in part on the calibration code, compensating for the variation in the reagent when performing the method of determining the analyte concentration of the analyte in the sample.

* * * * *